United States Patent [19]
Cutler et al.

[11] Patent Number: 5,155,045
[45] Date of Patent: Oct. 13, 1992

[54] USE OF MALE ESSENCE TO ALTER FEMALE ENDOCRINE RESPONSE

[75] Inventors: Winnifred B. Cutler, Haverford; George Preti, Horsham; Celso R. Garcia, Merion, all of Pa.

[73] Assignee: Trustees of the University of Penn., Philadelphia, Pa.

[21] Appl. No.: 857,935

[22] Filed: Apr. 30, 1986

Related U.S. Application Data

[63] Continuation-in-part of Ser. No. 694,947, Jan. 25, 1985, abandoned.

[51] Int. Cl.[5] .................. G01N 33/48; G01N 33/50
[52] U.S. Cl. ............................. 436/65; 436/128; 436/131; 436/906; 436/817; 514/169; 514/170; 514/177; 514/178; 514/179; 514/182
[58] Field of Search ............... 424/105; 514/169, 170, 514/177-179, 182; 436/817, 65, 128, 131, 906

[56] References Cited

U.S. PATENT DOCUMENTS

| | | | |
|---|---|---|---|
| 3,986,494 | 10/1976 | Preti et al. | 128/2 R |
| 4,010,738 | 3/1977 | Preti et al. | 128/2 R |
| 4,119,089 | 10/1978 | Preti et al. | 128/2 R |
| 4,385,125 | 5/1983 | Preti et al. | 436/65 |
| 4,670,401 | 6/1987 | Cutler et al. | 436/65 |

OTHER PUBLICATIONS

*The Merck Index*, 10th ed., p. 666 (1983).
Stedman's Medical Dictionary, 24th ed. Williams and Wilkins, Baltimore, 1982, p. 66.
Astwood in *The Pharmaceutical Basis of Therapeutics*, Edited by Goodman and Gilman, 3rd ed., The Macmillan Co., N.Y. 1965, p. 1576.
R. F. Vollman, "The Degree of Variability of the Length of the Menstrual Cycle in Correlation with Age of Woman", *Gynaecologia* 142(5):310–314 (Nov. 1956).
M. K. McClintock, "Pheromonal Regulation of the Ovarian Cycle: Enhancement, Suppression and Synchrony", *Pheromones and Reproduction in Mammals*, Edited by J. G. Vandenbergh New York, Academic Press, pp. 113–149 (1983).
M. K. McClintock, "Estrous Synchrony: Modulation of Ovarian Cycle Length by Female Pheromones", *Physiol. Behav.*, 32:701–705 (1984).
M. K. Izard, "Phermones and Reproduction in Domestic Animals", *Pheromones and Reproduction in Mammals*, edited by J. G. Vandenbergh New York, Academic Press, pp. 253–281 (1983).
Izard et al, "Priming Pheromones From Oestrous Cows Increase Synchronization of Oestrus in Dairy Heifers After PGF-2αInjection", *Reproduction Fertility*, 66:189–196 (1982).
M. K. McClintock, "Menstrual Synchrony and Suppression", *Nature*, 229:244–245 (Jan., 22, 1971).

(List continued on next page.)

Primary Examiner—F. T. Moezie

[57] ABSTRACT

A novel method for treating a human female is disclosed comprising the step of exposing the nasal region of said female to at least a portion of the axillary secretions of a human male. This exposure is preferably continued in amounts and for a duration which are effective to significantly alter an endocrine related characteristic, such as the menstrual cycle length, of that female. In particular, the portions of male axillary secretions to be exposed to the female preferably comprise one or more compounds such as androstenol, dehydroepiandrosterone, and/or a compound or compounds exhibiting a burnt heavy axiallary-like odor which elutes at about 50 minutes as shown on the FID response curve of FIG. 3B. Studies show that pooled male donor secretions are effective to alter aberrant menstrual cycles, particularly those exhibiting luteal phase defects such that they become presumptively fertile menstrual cycles having durations of about 29.5±3 days. Symptoms of perimenopause, such as hot flashes, night sweats and irregular menstrual cycles, are also treatable using the methods of this invention, which tend to promote female endocrine regularity and longevity.

18 Claims, 5 Drawing Sheets

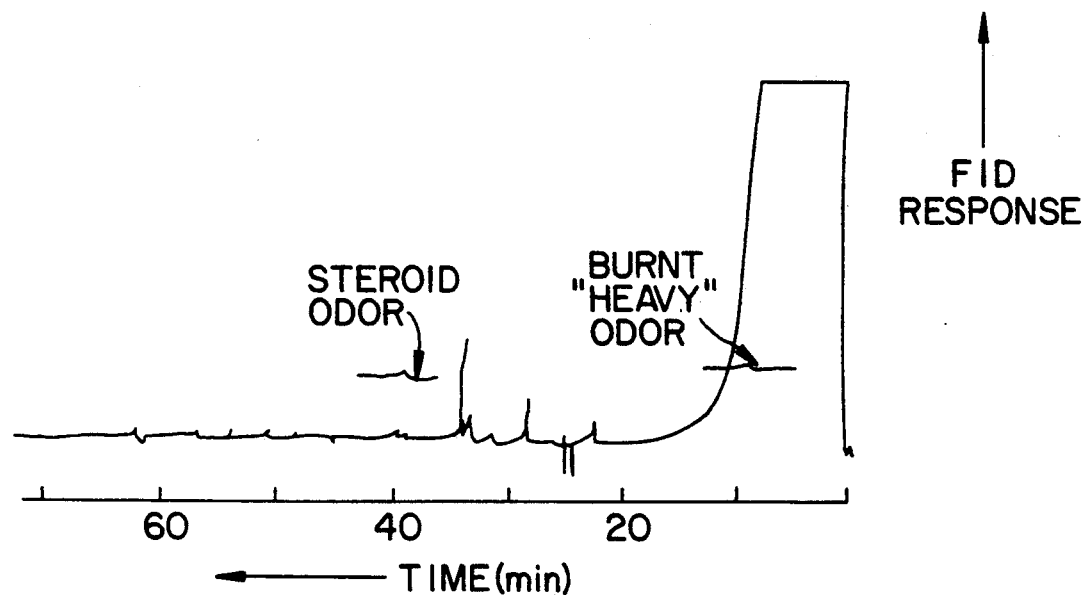
F I G. 3A
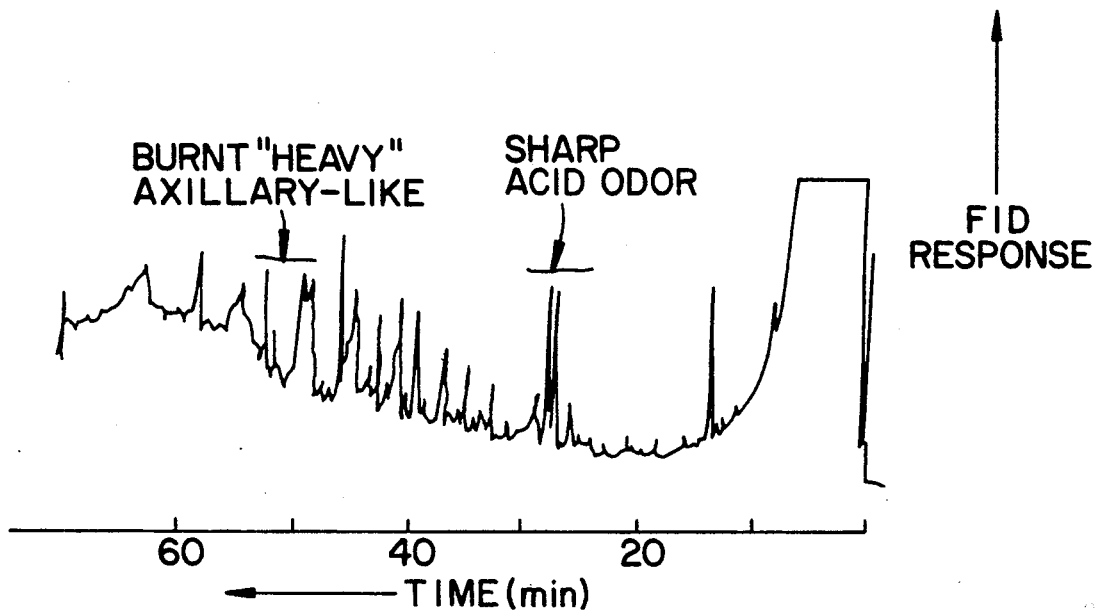
F I G. 3B

USE OF MALE ESSENCE TO ALTER FEMALE ENDOCRINE RESPONSE

CROSS-REFERENCE TO RELATED PATENTS AND APPLICATIONS

This application is a continuation-in-part of U.S. Ser. No. 694,947, filed Jan. 25, 1985, entitled "The Use of Male Essence, Including Androstenol and Dehydroepiandrosterone Sulfate to Treat Luteal Phase Defects and Failure to Ovulate in Human Females", now abandoned.

The present application is related to U.S. Pat. Nos. 3,986,494 entitled "Method of Predicting and Detecting Ovulation" (Preti and Huggins); 4,010,738, entitled "Method of Predicting and Detecting Ovulation" (Preti and Huggins); 4,119,089, entitled "Method of Predicting and Determining Ovulation by Monitoring the Concentration of Volatile Sulfur-Containing Compounds Present in Mouth Air" (Preti, Huggins and Tonzetich); and 4,385,125, entitled "Method Detecting Ovulation by Monitoring Dodecanol Concentration in Saliva" (Preti, Kostelc, Tonzetich and Huggins), each of which patents is hereby incorporated by reference as if fully set forth herein.

This application is also related to U.S. application 695,053, filed Jan. 25, 1985, entitled "Axillary Androstenol and Dehydroepiandrosterone as Fertile Period Onset Indicators" Attorney Docket MON-40), now abandoned, which application is hereby incorporated by reference as if fully set forth herein.

This application is also related to U.S. application 694,946, filed Jan. 25, 1985, entitled "Method Using Pooled Female Axillary Essence From Multiple Donors to Alter Menstrual Cycle Timing", (Attorney Docket MON-38), now abandoned, which application is hereby incorporated by reference as if fully set forth herein.

BACKGROUND OF THE INVENTION

The present invention relates to the field of reproductive biology, and more particularly to methods used by reproductive biologists, gynecologists and/or obstetricians to predict in human females the probability that a given menstrual cycle type is presumptively fertile or infertile, the timing of the menstrual cycle and/or the onset of the fertile period, and/or the time of ovulation. The field of the present invention includes the field of detection and diagnosis of ovulation in human females through the detection of secondary characteristics occurring during or at the time of ovulation, and more particularly, to the identification and detection of such secondary characteristics as they appear in human females. It further relates to menopause and perimenopause, and methods of treating the symptoms thereof.

For many years there has been a need to detect and diagnose the precise time of ovulation in a given female mammal. It can be of great importance, for example, to pinpoint the time of ovulation to ensure that fertilization occurs or to prevent conception. Alternatively, it may be important for other medical reasons to diagnose ovulation To some extent, methods of diagnosing ovulation are disclosed in the above-identified related patents. Additionally, the occurrence of ovulation can be established with some certainty through various prior art methods. For a review of many of the known surgical, clinical, biochemical or hystological techniques for diagnosing ovulation, please refer to the descriptions appearing in the above-mentioned related patents and patent applications, particularly to columns 1-5 of U.S. Pat. No. 4,119,089.

Perhaps the most popular and widely used method of estimating the time of ovulation relies upon the graphic recording of the waking temperature at basal conditions (hereinafter referred to as the BBT method). Using this method a dedicated woman with uniform daily habits can determine the time of ovulation within two days after its occurrence. In recording the basal body temperature, a rise in temperature is commonly associated with the beginning of the luteal phase, but can vary from the actual time of ovulation by as much as 72 hours. FIG. 1 of U.S. Pat. No. 4,119,089 illustrates a theoretical basal body temperature chart showing a biphasic cycle having a lowered body temperature during the follicular phase, and a sustained raised body temperature during the luteal phase.

Another technique which is commonly used to determine the time of ovulation in human females is the charting of concentrations of certain hormones appearing in the blood. In humans, a preovulatory rise in serum estrogens coupled with a sharp rise in luteinizing hormone (LH) levels as determined by radio-immunoassay of serially drawn blood samples, is perhaps the most accurate indicator of impending ovulation. Ovulation most likely occurs 12-24 hours after maximum LH levels. A subsequent persistent increase in levels of serum progesterone indicates that ovulation has occurred. Since these determinations are expensive and not widely available, clinical parameters such as BBT parameters are most often used to determine the time of ovulation.

The field of the present invention also relates to methods of predicting the onset of the fertile period. It is generally accepted that the maximum survival function of spermatozoa capable of fertilizing an ovum is approximately three days following coitus. Although theoretically any coitus prior to ovulation entails a certain risk of pregnancy, as a practical matter, abstinence from unprotected sexual intercourse for at least 3 days (preferably up to 5 days) prior to ovulation is generally considered sufficient to avoid pregnancy. It is generally recognized that a human ovum is (in vivo) fertilizable for about 12 hours and certainly for no more than 1 day following ovulation. The human fertile period, then, is made up of no more than 4 to 6 days out of the entire menstrual cycle. If it were possible to accurately predict this fertile period, in order to avoid pregnancy it would only be necessary to abstain from unprotected intercourse or use alternate birth control methods during that 4-6 day "fertile period" rather than for the entire menstrual cycle.

Notwithstanding the methods of the aforementioned related patents, the only technique yet widely used for "predicting" the fertile period of a female is the method which relies upon basal body temperature determination of ovulation in a plurality of preceding cycles to determine the expected time of ovulation for future cycles. This method is not really directed to ascertaining the precise fertile period for a given cycle, but rather is intended to identify a period during which coitus is statistically likely to produce pregnancy. Based on calendar records of 21,499 menstrual cycles experienced by 592 healthy women living in Switzerland, 9.7% of all menstrual cycles range in length from 6-23 days, 80.1% into the range from 24-34 days, and another 10.2% cover the remainder of menstrual cycles from 35 to 409 days in length. The modal cycle length of the cycle of 28 days duration and the average cycle length amounts to 29.2 days. See "The Degree of Variability in the Length of the Menstrual Cycle in Correlation with Age of Woman", by R. F. Vollman, *Gynaecologia*, 142(5): 310-314 (November 1956). Since this information is based upon past performance, and since the time of ovulation varies markedly between different individuals as well between cycles of a given individual, the period for abstinence must be long enough to considerably reduce the possibility of pregnancy. As explained in U.S. Pat. No. 4,119,089, taking into account the variability in menstrual cycle length, even the most regular women probably need to abstain from unprotected coitus for more than one-third of the total menstrual cycle in order to avoid pregnancy. Accordingly, a long felt need exists for methods of more accurately predicting or detecting the onset of the fertile period for a given cycle, such that coitus can be avoided, or other contraceptive methods employed, during the fertile period of that cycle.

The present invention also relates to the field of mammalian chemical communication, and more particularly to research involving mammalian pheromones. It has long been known that the estrus cycles of certain mammalian species are affected by pheromones and that their estrus cycles may be artificially manipulated. For examples, estrus cycles of rats can be manipulated through the use of odors collected from females during specific phases of the estrous cycle. See McClintoc M. K., "Pheromonal Regulation of the Ovarian Cycle: Enhancemen , Suppression and Synchrony", *Pheromones and Reproduction in Mammals*, edited by J. G. Vandenbergh, New York: Academic Press, pp. 113-149 (1983) and McClintock, M. K., "Estrous Synchrony: Modulation of Ovarian Cycle Length by Female Pheromones", *Physiol. Behav.* 32:701-705 (1984). In addition, preovulatory cervical mucus mixed with water and sprayed into the noses of a group of female Holstein cows advanced and synchronized the time of estrous. See Izard, M. K. "Pheromones and Reproduction in Domestic Animals", *Pheromones and Reproduction in Mammals*, edited by J. G. Vandenbergh, New York: Academic Press, pp. 253-281 (1983) and Izard, M. K. and Vandenbergh, J. G., "Priming Pheromones From Oestrous Cows Increase Synchronization of Oestrus in Dairy Heifers After PGF-2 Injection", *J. Reprod. Fert.* 66:189-196 (1982). Notwithstanding these and other reports of elaborate pheromonal systems in other mammals until now there has been no experimental evidence that pheromonal systems operate in humans.

More recently a number of studies have suggested the possibility that human odors act in a manner analogous to primer pheromones in animals and alter reproductive endocrinology. Although anecdotal reports of aphrodisiacs are as old as modern civilization, the possibility that human reproductive biology can be altered by pheromones was not considered seriously until McClintock published a report in 1971 that menstrual synchrony occurred among certain women attending a predominantly female university. In "Menstrual Synchrony and Suppression", Nature, 229:244-245 (Jan. 22, 1971) McClintock reported that "social interaction" can have a strong effect on the menstrual cycle of woman living together in a college dormitory. The McClintock study compared the dates of menstrual onset for roommates and close friends, and for living groups. McClintock reported that a significant increase in menstrual synchrony was found among roommates, among closest friends, and among roommates and closest friends combined. McClintock hypothesized that the synchrony could be due to some factor other than time spent with an individual such as the available food and/or synchrony of the moon. McClintock further speculated that synchrony might parallel the Whitten effect in mice in which suppression of oestrous in groups of females may be released by the introduction of a male mouse pheromone. McClintock suggested that synchrony might result from a pheromonal interaction of suppression among close friend groups, followed by a periodic release due to the presence of males on the weekend. McClintock stated:

"However, this would be insufficient to explain the synchrony which occurred among roommates and close friends but did not occur throughout the dormitory."

A further possible explanation advanced by McClintock was the awareness of menstrual cycles among friends, however a sample taken from the dormitory indicated that 47% were not conscious of their friends' menstrual cycles, and of the 53% who were, 48% were only vaguely aware. While McClintock was able to conclude that a significant factor in synchrony is that individuals in the group spend time together, McClintock was ultimately unable to state whether the mechanism underlying this phenomenon is pheromonal, mediated by awareness, or some other process, indicating that the question "still remains open for speculation and investigation". McClintock also explained:

"Exposure to males may not be the significant factor. It may be, for example, that those with longer cycles are less likely to spend time with males. However, many subjects spontaneously indicated that they became more regular and had shorter cycles when they dated more often. For example, one subject reported that she had a cycle length of six months until she began seeing males more frequently. Her cycle length then shortened to 4.5 weeks. Then, when she stopped seeing males as often, her cycle lengthened again. Whether this is due to a pheromone mechanism similar to the Lee-Boot effect in mice has yet to be determined." [Lee and Boot, *Acta physiol. Pharmacol Neerl.*, 5, 213 (1956)].

Subsequent investigators have also considered the effect on menstrual synchrony of females in different living conditions. In "Menstrual Synchrony in Female Undergraduates Living on a Coeducational Campus", *Psychoneuroendocrinology,* 5:245-252 (1980), Graham and McGrew report investigations of menstrual synchrony among female undergraduates living on a coeducational university campus. A significant trend toward synchrony was found for closest friends, but no significant effect occurred for neighbors or randomized pairs. Nor did any significant correlation emerge between cycle length, duration, duration of menstruation, or the amount and nature of social interaction with males. Graham and McGrew accordingly conclude that the amount of time individuals spend together, not similar living conditions, is the significant fact in synchrony. Graham and McGrew further conclude that the "how and why" of menstrual synchrony remain unknown, indicating that, as suggested by Rogal in "A Critical Evaluation of the Possibility of Higher Primate Reproductive and Sexual Pheromones", *Psychol. Bull.* 85:810-830 (1978), menstrual synchrony cannot be explained by any existing hypothesis other than a pheromonal one.

In 1981, Quadagno et al reported a tendency toward menstrual synchrony which was greatest between roommates and close friends. See Quadagno, D. M., Shubeita, H. E., Deck J. and Francoeur, D., "Influence of Male Social Contacts, Exercise and All Female Living Conditions on the Menstrual Cycle", *Psychoneuroendocrinol* 6:239-244 (1981). Casual exercise performed regularly was associated with longer menstrual cycles whereas spending "social time" with a male was reported not to have any effect on the length of the menstrual cycle for the women in the study. Noting McClintock's finding that "women seeing males less than 3 times a week experience significantly longer cycles than women who spent time with males more than 3 times per week", Quadagno nonetheless confirms Graham and McGrew's findings that no significant correlation exists between cycle length and the amount and nature of social interaction with males.

Most recently, Veith et al have reported that exposure to men has the capacity to shorten the menstrual cycle in women. See "Exposure to Men Influences the Occurrence of Ovulation in Woman", *Physiology and Behavior* 31:313-315 (1983). Veith et al report that women who spent two or more nights with men during a 40 day period exhibited a significantly higher rate of ovulation as determined by basal body temperature charts than those spending no or one nights. Cycle length was not effected by sleeping arrangements, and the frequency of sexual intercourse was said to be unrelated to either cycle length or likelihood of ovulation. The mechanism underlying this phenomenon was reported to be "unknown", but was "conjectured" to be pheromonal in nature. Veith et al thus conclude that "a significant variable contributing to the likelihood of ovulation are the number of nights a woman spends in the same bed with a man". Veith et al further conclude that cycle length "was not influenced by this factor", noting that the "lack of replication of the earlier [McClintock] study concerning the lengthening of cycles in those women with limited exposure to males is surprising". Veith suggests that the naturalistic conditions resulting from subjects being enrolled in a coeducational institution may provide participants with sufficient exposure to men so that their cycle length would not be unduly increased.

A number of studies have investigated the possible effect of underarm perspiration on menstrual synchrony. In 1977, Russell, Switz and Thompson reported on the effects of using the female axillary sweat of a single, so-called "driver" female as a stimulus towards menstrual synchrony. See "Olfactory Influences on the Human Menstrual Cycle" presented at the meeting of the American Association for Advancement of Science, San Francisco, June 1977 and published in *Pharmac. Biochem. Behav.* 13(5):1-2 (1980). Russell et al had female volunteers rub on their upper lips cotton pads containing the perspiration odor of a particular donor female. After four months the menstrual onset dates of the volunteers were significantly closer to that of donor female than were the cycles of the control group who received the application but not the odor. The particular female donor subject had a history of a very regular menstrual cycle of 28 days and no significant history of menstrual problems. She had demonstrated a previous experience of "driving" another woman's menstrual cycle on three separate occasions over three consecutive years, did not use underarm deodorant nor shave under her arms. These data showed that the mean difference from onset of the menstrual cycle of the subjects from the donor was 9.3 days in the pretreatment month and 3.4 days in the post treatment month for the experimental group, and that this change showed statistical significance over the control group. Russell et al thus conclude that "odors from one woman may influence the menstrual cycle of another and that these odors can be collected from the underarm, stored as frozen samples, for at least short periods, and placed on another woman." The experiment was further said to support the theory that odor is a communicative element in human menstrual synchrony, and that at least a rudimentary form of olfactory control of the hormonal system is occurring in humans in a similar fashion to that found in other mammals.

As Russell et al noted, it is possible that volatile substances are transferred to the nose even though the subject has no awareness of them. It is also possible that the mechanism of transfer in the Russell et al study did not involve the nose at all, but diffusion of chemical compounds through the skin which may occur when the sample was placed on the subject's upper lip.

Underarm sweat comprises secretions of the apocrine, eccrine and sebaceous glands. Analyses of apocrine secretion have shown the presence of protein (10%), cholesterol (1%) and two androgen steroids: androsterone sulfate and dehydroepiandrosterone sulfate (0.2%). The apocrine secretion as collected at the skin surface is odorless; however, incubation with the resident skin bacteria results in an odor profile unique to that organism. The micrococci bacteria give an "acid odor" to the secretion which has been characterized by head space analysis as isovoleric acid. See Labows, J. N. "Human odors—what can they tell us?", *Perfumer and Flavorist* 4:12-17 (1979). The diptheroid bacteria give a similar head space profile but the observed odor is the more distinct "apocrine (human) odor" usually associated with the axillary areas.

Similar correlations of odor quality and bacterial populations were found in vivo. The axillary microflora of 229 subjects have been characterized quantitatively and their results correlated with the type of donor found. Microccaceae were present in all subjects and were the dominant organism when a faint or acid odor was noted. The aerobic diptheroids were found in 85% of the males and 66% of the females and were associated with a pungent, apocrine odor. There were no significant differences related to handedness or presence of axillary hair. See Leyden, J. J., McGinley, K. J., Hoelzle, E., Labows, J. N. and Kligman, A. M., "The Microbiology of the Human Axillae and its Relation to Axillary Odors", *J. Invest. Dermatol.* 77:413-416 (1981).

The "apocrine odor" is similar to that of androst-16-en-3-one. See Labows, J. N. 1979, supra. Neither this steroid nor androst-16-en-3-ol, a musky odorant are present in original odorless secretion but they have been shown to be present in axillary sweat. See Bird, S. and Gower, D. B., "Axillary 5 -androst-16-en-3-one, Cholesterol and Squalene in Men: Preliminary Evidence for 5 -androst-16-en-3-one Being a Product of Bacterial Action", *J. Steroid Biochem.* 17:517-522 (1982); Bird, S.

and Gower, D. B., "Measurement of 5-androst-16-en-one in Human Axillary Secretions by Radioimmunosassary", *J. Endocrinol.* 85:80-90; and Brooksbank, B. W. L., Brown, R. and Gustafsson, J. A., "The Detection of 5-androst-16-en-3 ol in Human Male Axillary Sweat", *Experientia* 30:864-865 (1974). In experiments in which axillary bacteria where incubated with sterile apocrine sweat, typical pungent male odor was produced only with aerobic diptheroids. This included both isovoleric acid and another component which was pungent. The odor is similar in character to androst-16-en-3-one and this material has been detected on axillary pads using radio-immunoassay procedures. See Bird, S. and Gower D. B. supra. Studies of extracts of odorous cultures of diptheroids grown on apocrine secretion by GC/MS as yet have not revealed detectable levels of androstenone. It is reasonable to assume, however, that further studies will reveal them since they are detected in axillary washings. Personal Communication, 1984. Dr. J. N. Labows, Monell Chemical Senses Center.

Apart from the above-mentioned data, Graham et al describe the remaining evidence for pheromonal communication of a human female's hormonal status as being "largely circumstantial and fragmentary". For example, Graham et al cite work on short-chain fatty acids in human vaginal secretions; vaginal odors; odor discrimination studies; effects of alleged human pheromonal preparations on subject performance; and scent-marking experiments in public places using androstenone, a mammalian pheromone, which is said to alter spontaneous behavior. See for example, Clark, Klassnick and Watson, "Human Responses to Scent-Marking with the Putative Pheromone Androstenone" (1978) (unpublished manuscript cited in Graham et al supra).

In addition to the above, numerous publications discuss various factors such as lunar synchrony which may effect the length of the human menstrual cycle. See "The Menstrual Cycle" by Rudolph V. Vollman, M. D., Vol. 7, *Major Problems in Obstetrics and Gynecology*, edited by Emmanuel A. Freidman, M. D.; Treloar, "Variation of the Human Menstrual Cycle Through Reproductive Life", *International Journal of Fertility*, 12 (1); 77-126 (1967). More recently, Winnifred Berg Cutler has reported upon the relationship between the lunar and menstrual cycle phases. See "Lunar and Menstrual Phase Locking", by Winnifred Cutler, *American Journal of Obstetrics and Gynecology* 137:834 (1980). In this study, reference is made to data showing the mean and median of sample menstrual cycle data to be 29.5 days, and notes the coincidence of this cycle length and the 29.5 day lunar cycle. Cutler has noted that 98% of the cycles of 29.5±1 day in length are ovulatory, and has suggested that ovulation may frequently occur during the new moon part of the cycle.

In addition to the factors discussed above, sexual behavior has often been discussed as a factor which contributes to the rhythm of the human cycle and subsequent fertility. Cutler has published extensively on the possible interrelationship between infertility and first coitus, sexual behavior frequency and menstrual cycle length, short hyperthermic phases and sporadic sexual behavior in woman, and relationships between estrogen level, hot flashes and sexual behavior in perimenopausal woman. See Cutler et al "Infertility and Age at First Coitus; A Possible Association", *J. Biosoc. Sci.* 11:425-432 (1979); Cutler et al, "Sexual Behavior Frequency and Menstrual Cycle Length in Mature Premenopausal Women", *Psychoneuroendochrinology* 4:297-309 (1979); Cutler et al, "Luteal Phase Defects: A Possible Relationship Between Short Hyperthermic Phase ad Sporadic Sexual Behavior in Women", *Hormones and Behavior* 13:214-218 (1979); Cutler et al, "Sporadic Sexual Behavior and Menstrual Cycle Length in Women", *Hormones and Behavior* 14:163-172 (1980); Cutler et al, "The Psychoneuroendocrinology of the Ovulatory Cycle of Woman, A Review", *Psychoneuroendocrinology* 5:1980; and Cutler et al, "Relationships Between Estrogen Level, Hot Flashes and Sexual Behavior in Perimenopausal Women", *Neuroendocrinology Letters* 5:185 (1983).

In addition to the Vollman and Treloar studies discussed above, which clearly suggest that women whose cycles approach a 29 day span have the highest likelihood of a fertile cycle, Cutler et al have demonstrated that women who have regular weekly, heterosexual activity have menstrual cycles of about 29 days, whereas women who either have sporadic sexual activity or who are celibate tend to have a higher frequency of aberrant length cycles (25 or less or 34 or more days). These studies suggest that luteal phase defects (shortened hyperthermic phases) and sporadic sexual activity in the luteal phase are associated in a population of infertility patients. Delayed age of first coitus is also associated with a higher frequency of subsequent infertility.

Even more recently, Cutler et al have evaluated whether self stimulation (masturbation), coitus, and or heterosexual genital stimulation by a man without coitus, could be differentiated in terms of their relative association to fertility. In this study presumptive fertility (P. fertility) was evaluated by the menstrual cycle length and by analysis of basal body temperature charts. It was found that weekly heterosexual behavior is consistently associated with menstrual cycle lengths of 29.5±3 days and that self stimulation behavior does not show a similar association between weekly behavior and circa 29 day menstrual cycle lengths. Woman who report regular weekly sex with men are found to have a greater incidence of presumptively fertile menstrual cycles than those who report sporadic sexual activity. In the Cutler et al study the chief problem associated with less frequent sexual activity is less a failure to ovulate but rather a short luteal phase. A fertile menstrual cycle requires both an ovulation and an adequately long luteal phase to ensure sufficient time and steroid output to prepare the endometrium for implantation. The Cutler et al study shows that sexually active women who have regular, stable patterns of sexual activity have significantly more fertile type cycles than women of the same age who have sporadic patterns of sexual activity. The hypothesis that normalization of the menstrual cycle is due to something more than genital stimulation, but requires the presence of a male partner, is consistent with the suggestions of McClintock, the data of Quadagno, and numerous studies and observations conducted with non-human primates and other mammals, some of which suggest the presence of a male or his odors are important in regulating cyclicity and/or fertility.

The influence of mammals or their odors on the estrous cycles of other female conspecifics has been well-documented in recent studies employing infra-human mammals. See McClintock, M. K. 1983, supra., McClintock, M. K. 1984 supra., Izard, M. K. 1983, supra., and Izard, M. K. and Vandenberg, J. G. 1982, supra. For example, the estrous cycle of rats can be manipulated through the use of odors collected from females during specific phases of the estrous cycle. In several rodent species, exposure to the odors of urine or cage bedding of males can promote estrous or stimulate ovulation. In some infra-human primates, males can influence cycle length. Female baboons denied a mating showed significantly longer cycles and rhesus monkeys showed a summer amenorrhea two to four months after a male decrease in sexual potency.

Notwithstanding what is known on this topic, the problems of unwanted fertility and unwanted infertility remain among the most important of human concerns. Since a reasonable percentage of infertility may stem from conditions reflected in menstrual cycles of aberrant lengths, methods for adjusting the lengths of those menstrual cycles have a good likelihood of creating presumptively fertile $29.5\pm3$ day cycles. Similarly, for those women choosing to avoid pregnancy, the provision of a physiologically compatible method for stimulating infertile-type cycles would be of utmost utility. Finally, improved methods for regulating the timing of the menstrual cycle could improve the predictability of the occurrence of the fertile period and/or menstruation and expand the range of therapeutic possibilities for addressing both fertility and infertility problems.

The present invention also relates to perimenopause the years proceeding the menopause when menstrual cycle habits and endocrine milieu are changing. Before the menopause occurs with its final cessation of menses (usually around the age of 51), a seven year period of perimenopausal transition is common. This "perimenopausal" stage is characterized by changes in menstrual cycle length and bleeding pattern. Commonly, the cycles become unusually long (more than 33 days) or short (less than 26 days). Treloar et al "Variations of the Human Menstrual Cycle Through Reproductive Life", *International Journal of Fertility*, 12: 77–126 (1967); Vollman, "The Menstrual Cycle", Vol. 7 in *Major Problems in Obstetrics and Gynecology*, W. B. Saunders, Philadelphia; Treloar, "Menstrual Cyclicity and the Premenopause", *Maturitas* 3:249–264 (1981). Additionally, changes often develop in the amount or duration of flow. Metcalf, "Incidence of Ovulatory Cycles in Women Approaching the Menopause", *Journal Biosoc Sci*, 11:39–48 (1979); Rutherford, "The Menopause", *NZ Med J*, 87:251–253 (1978). Although some perimenopausal sequelae (characteristics) have been well characterized, including hot flashes, emotional liability, and the inception of osteoporosis, less well established are the patterns of sexual response and sexual behavior changes in this transition stage. Cutler et al "Sexual Behavior, Steroids, and Hot Flashes are Associated During the Perimenopause", *Neuroendo L*, 5:185 (1983); Kupperman et al "Contemporary Theory of the Menopausal Syndrome", *JAMA*, 171:1627–1637 (1959) and McCoy et al, "A longitudinal Study of the Effects of Menopause on Sexuality", *Maturitas* 7:203–210 (1985).

There is a general consensus within the biomedical literature that the declining capacity for sexual response coincides with the declining levels of estrogens occurring at menopause. For a detailed literature review, see Cutler and Garcia, *Medical Management of Menopause and Premenopause: Its Endocrinologic Basis*, J. B. Lippincott, Philadelphia, PA (1984). Outside the medical literature, women researchers have published data to suggest no loss of arousal during this period. See Cutler et al, *Arch. Sex. Behavior* (in press). Previous reports have shown that weekly coital frequency behavior is distinguished from less than weekly coital behavior; women who have weekly sex with men show cycle length characteristics and basal body temperature (BBT) patterns reflective of a more fertile endocrine milieu. It has previously been reported that weekly sex is associated with an increased incidence of 29 days cycles and fertile BBT charts in two populations: gynecologically mature young women (see Cutler et al, "Sexual Behavior Frequency and Menstrual Cycle Length in Mature Premenopausal Women", *Psychoneuroendocrinology*, 297–309 (1979) and infertile women (Cutler et al), "Luteal Phase Defects: A Possible Relationship Between Short Hyperthermic Phase and Sporadic Sexual Behavior in Women", *Hormones and Behavior*, 13:214–218 (1979). In perimenopausal women, weekly sex is associated with a reduced incidence of hot flashes (Cutler et al, "Sexual Behavior, Steroids, and Hot Flashes are Associated During the Perimenopause", *Neuroendo L*, 5:185 (1983); McCoy et al, "Relationships Among Sexual Behavior, Hot Flashes and Hormone Levels in Perimenopausal Women", *Arch Sex Behavior*, 14(5):385–394 (1985).

Notwithstanding our current knowledge in this area, a need still exists for a physiologically acceptable method for altering and/or regulating female endocrine-related characteristics such as menstrual cycle length, the timing of menopause, and the occurrence of perimenopausal symptoms.

SUMMARY OF THE INVENTION

The present invention provides a novel method for altering and/or regularizing human female endocrine-related characteristics, such as the length of the menstrual cycle. For example, applicants have discovered that the axillary secretions of males, when exposed to the nasal region of females with a history of aberrant cycle lengths ($<26$ or $>33$ days) tend to induce normal, presumptively fertile menstrual cycles having lengths of about $29.5\pm3$ days. Applicants have demonstrated that, as compared to controls receiving only solvent (ethanol) applications, woman receiving male axillary extracts experienced more regular cycles, and, based on BBT data, more presumptively fertile cycles.

In accordance with the preferred embodiment of the present invention, the male donor axillary secretions should be exposed to the nasal region of the female for a duration and in amounts effective to significantly alter and/or regularize the expected cycle length of that female. Such exposure should preferably be accomplished through periodic applications of male donor extract of the axillary secretions of one or more males. The method is particularly useful in treating woman exhibiting aberrant menstrual cycles which are either monophasic, or which have lengths 26 days or less or 33 days or more. Menstrual cycles of 26 days or less are often indicative of luteal phase defects which are associated with presumptively infertile cycles. Accordingly, the present method is particularly adapted for increasing the presumptive fertility of those cycles by exposing a female having a menstrual cycle exhibiting a luteal phase of less than 12 days to the subject male donor axillary secretions for a period of time sufficient to increase the length of the luteal phase of the that menstrual cycle to at least 12, and preferably to about 14–16 days.

In accordance with a further embodiment of the present invention, male axillary secretions or extracts are exposed to the nasal region of perimenopausal women to treat endocrine-related characteristics such as the symptoms of menopause. The promotion of menstrual regularity in the late cycling years, which are most prone to irregularity, should inhibit menopausal symptoms and promote endocrine longevity.

It is theorized that male axillary secretions naturally stimulate the female endocrine system to produce relatively higher levels of estrogen. It is now clear from the literature and our own studies that stimulation of the female endocrine system, as for example by having at least weekly sex with a man, increases estrogen levels and decreases the symptoms of menopause. The use of estrogen to reduce menopausal symptoms and to delay the menopause is also well known. See Treloar, "Variations of the Human Menstrual Cycle Through Reproductive Life,", *J. Reprod. Fertil*, 12:77-126 (1967); Treloar, "Menstrual Cyclicity and the Premenopause", *Maturitas* 3: 249-264 (1981). It is also known that increased levels of sexual behavior leads to a reduction in perimenopausal symptoms McCoy et al, "Relationships Among Sexual Behavior, Hot Flashes and Hormone Levels in Perimenopausal Women", *Archives of Sex Behavior*, 14(5):385-394, cover date April, 1985, received at the University of Pennsylvania library, May 25, 1985. As reported in Cutler et al, "Sexual Behavior and Steroid Levels Among Gynecologically Mature Premenopausal Women", *Fertil & Steril* (April, 1986), women having at least weekly sex with men exhibit higher levels of estrogen than women who do not. It has now also been determined that perimenopausal women who have low estradiol levels (less than or equal to 35 pg/ml) tend to have reduced coital activity. See, Cutler et al "Perimenopausal Sexuality", *Archives of Sexual Behavior* (in press). This is consistent with previous reports showing that the age of menopause of spinsters is earlier (46.9 years) than that of widows (47.7 years), which in turn is earlier than that of married women (48.9 years). See C. C. Norris, "The Menopause", *Am. J. Obstet.* 41:203-215 (1910).

As seen from the data reported herein, the application of male axillary secretions to the nasal region of women surprisingly has the same or nearly the same effect on the cycles of those women as weekly sex with men. Accordingly, for those women who do not prefer synthetic hormone treatments and/or for whom weekly sex with a man is not an acceptable alternative, the methods of the present invention may be preferred for altering female endocrine-related characteristics such as perimenopausal symptoms and/or menstrual cycle regularity.

Accordingly, the present invention provides a novel material for application to the human body- comprising axillary secretions of at least one human male donor, which material may be provided in a kit for altering female endocrine-related characteristics. The subject kit should comprise a series of medicaments, each of which contains at least a portion of the axillary secretions of a human male donor, whereby the medicaments may be administered and/or exposed periodically to the nasal region of the female.

Accordingly, a primary object of the present invention is a method for altering the length of the menstrual cycle of a human female and regularizing it towards a normal 29.5±3 day menstrual cycle length.

A further object of present invention is the provision of the method for altering or regulating the length of the menstrual cycle of a human female to produce a greater incidence of presumptively fertile menstrual cycles.

Another object of the present invention is the treatment of perimenopausal symptoms.

Another aim of the present invention is the extension of female endocrine longevity.

A further aim of the present invention is the provision of a novel method for treating human females exhibiting luteal phase defects.

A further aim of the present invention is the provision of a method for improving the fertility of a human female.

Another aim of the present invention is the provision of a kit for altering the length of the expected menstrual cycle of a human female.

These and other objects of the present invention will become apparent from the following, more detailed description.

BRIEF DESCRIPTION OF THE DRAWINGS

FIG. 3 are gas chromatographic, profiles in which the Flame Ionization Detector (FID) responses are presented in the vertical axis and time is presented in the horizontal axis. This figure illustrates odors which elute when the extracts are chromatographed using different liquid phases.

FIG. 3A shows the chromatogram on a non-polar silica phase (CP SIL-8).

FIG. 3B shows the chromatogram on a polar phase (CP-57 WAX).

DESCRIPTION OF THE PREFERRED EMBODIMENTS

Figure 1A:
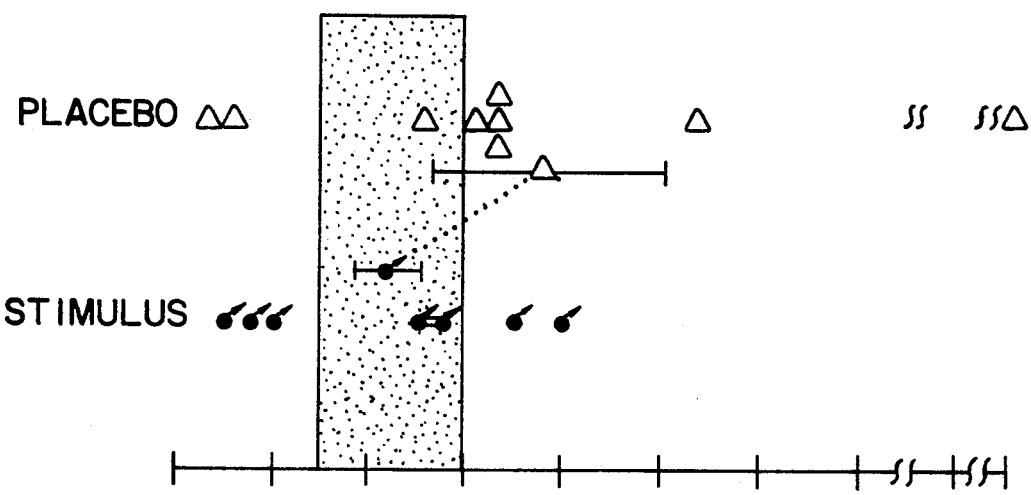
FIG. 1 shows the first cycle length (1A) and last cycle length (1B) of all subjects receiving male axillary extract stimulus as compared to subjects receiving only a placebo.

The present invention provides a novel method for altering female endocrine-related characteristics. The studies reported herein are believed to be the first systematically designed, prospectively conducted, double-blind research which demonstrate that male axillary secretions can influence female endocrine events. As used herein, the term "female endocrine-related characteristics" refers to those events or symptoms which are susceptible of statistically significant clinical or analytical diagnosis and which are under the control or influence of the female endocrine system. Such characteristics include the length, regularity and longevity of the menstrual cycle and perimenopausal or menopausal symptoms including hot flashes and night sweats. They further include levels of circulating hormones such as estrogen (estradiol).

In order to investigate potential mechanisms controlling the association between heterosexual activity and menstrual cycle length, and in light of the non-human literature suggesting that a chemical signal from males could be involved, it was investigated whether an extract from the male axillary region would be a sufficient stimulus to induce presumptively fertile type cycles.

Axillary secretions were collected from three male volunteers (age 41, 35 and 32). Each was engaged with a heterosexual relationship and had large numbers of lipophilic diptheroids in his axillary region. See Labows, J. N. 1979, supra. and Leyden, J. J., McGinley, K. J., Hoelzle, E. Labows, J. N. and Kligman, A. M. 1981, supra. In addition during the three months in which they collected sections they were required to (1) not use deodorant, deodorant soap or perfumes in the axillary region and (2) wash once in the morning with Ivory soap. Secretions were collected on 4 inch×4 inch cotton pads which had previously been extracted, autoclaved, dried and wrapped in solvent extracted foil. See Preti, G. and Huggins, G. R., "Cyclic changes in Volatile Acidic Metabolites of Human Vaginal Secretions and their Relation to Ovulation", *J. Chem. Ecol.* 1:361–376 (1975). Each donor wore a pad in each axilla three times a week during a six to nine hour period which was most convenient for him. Each day after removal, the pads from any one donor were placed in an individual acid-cleaned-glass-jar and frozen at $-60°$ C. until extraction. Secretions were collected three times a week from each donor for a 12 week period. Preparation of extract was conducted after all pads had been collected and frozen. Batches of glass jars were grouped consecutively according to the day received. Six to eight jars containing pads from all three individuals were used to prepare each batch of pooled extract. A total of 14 separate batches were prepared in this manner. All pads from each batches were placed in a glass column and allowed to soak in doubly distilled ethanol (15 ml/pad) for one hour. The ethanol was allowed to drain from the column through a PTFE (Teflon) stop cock and the pads were squeezed with a PTFE (Teflon) disk. Recovery approached 66% of the ethanol added to the pads. Presumably the remaining 34% remained within the pads. The ethanol extracted stimulus batches were then stored at $-60°$ C.

Subsequently, 15 women, varying in age from 19 to 22 and one aged 30 were enrolled in and completed the study All met the following criteria: "Gynecological maturity" (as defined by Treloar et al as menstruating for at least 7 years), nulliparous, unmarried, not currently (nor within the last months) using oral contraceptives nor an IUD, and a willingness to make daily entries of basal body temperature (BBT) and sexual behavior. Each potential subject who indicated her interest in participating was asked whether she thought she had short cycle ( 26 days) normal type cycle (29.5±3 days) or a long cycle (33 days). Those who indicated they had an aberrant length cycle (25 or less, or 34 or more days) were included in this study; those who indicated normal type cycles (29.5±3 day) were diverted to the study which is reported in connection with the aforementioned related patent application concerning the use of female essence to alter the timing of the menstrual cycle. In addition, all subjects agreed to provide blood samples for steroid analysis during three days of one week in the luteal phase of the last menstrual cycle studied. A complete history and physical exam was performed on each subject. This screening process for possible pathologies which might influence the length of the menstrual cycle failed to find any. Each subject was provided with basal body temperature (BBT) charts, BBT thermometers and a calendar card to record sexual behavior. Instructions for their use were given by a technician who was blind to the purpose of the study. Subjects were unaware of the true nature of the stimuli and were told only that they were receiving a "natural fragrance" extracted into ethanol. Thus the study was double-blind. Subjects were randomly assigned to group A (axillary extracts/ethanol) or group B (blank/ethanol). The average age of group A was 20 while the average age of the B group was 22. Application of the stimuli began in September, 1983, but because of individual variation in menstrual patterns any particular woman could enter the study at any point within her cycle.

Subjects came into the laboratory three times each week for 13.5±1 weeks for application of the stimuli (male extract or placebo). Each morning aliquots of the previously frozen stimuli were removed and allowed to warm to room temperature for 30 minutes. Individual 5 milliliter samples were removed via pipet and placed in separate vials for transport to the laboratory where the stimuli were applied. One half milliliter of the stimuli (axillary extract or placebo/ethanol) was pipeted onto a clean 4 inch×4 inch cotton pad. The technician rubbed the contents of the pad on the upper lip of the subject and instructed her not to wash the area for at least 6 hours.

Figure 1B:
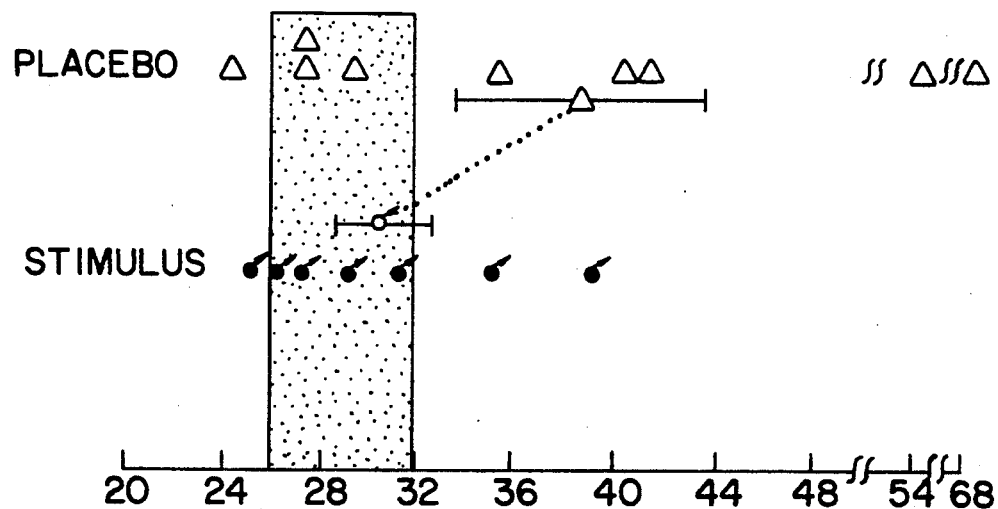

FIG. 1 shows the first cycle length (1A) and last cycle length (1B) of all subjects receiving stimulus. There was significantly less variance in cycle length for women receiving male stimulus then for women receiving the placebo (first cycle $F_{8,6}=5.97$, p less than 0.025; last cycle $F_{8,6}=8.09$, p less than 0.025). There was no over all difference in mean cycle length although a trend for this was evident by the last cycle ($t=1.45$, p less than 10).

Figure 2A:
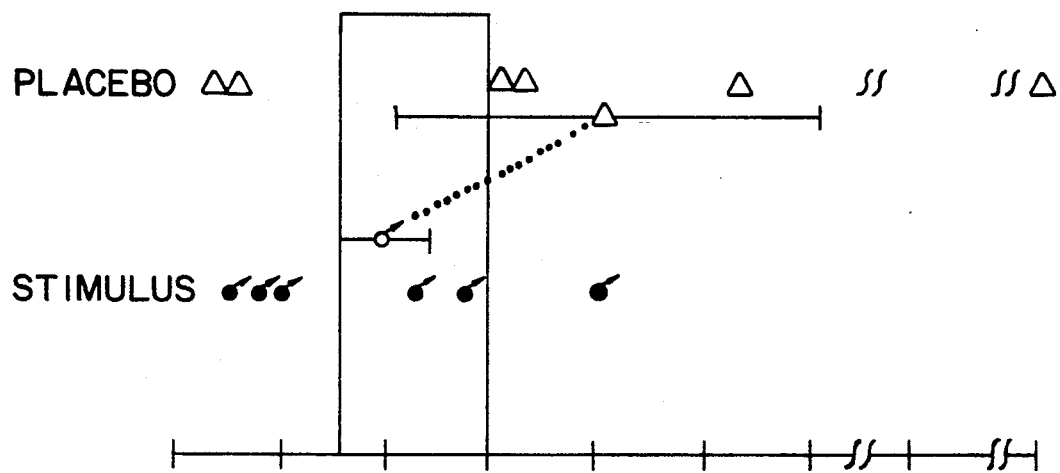
FIG. 2 is a chart in which data for women having weekly sexual activity was removed from the data set of FIG. 1, which shows the effect of the male extract stimulus on cycle length.
Figure 2B:
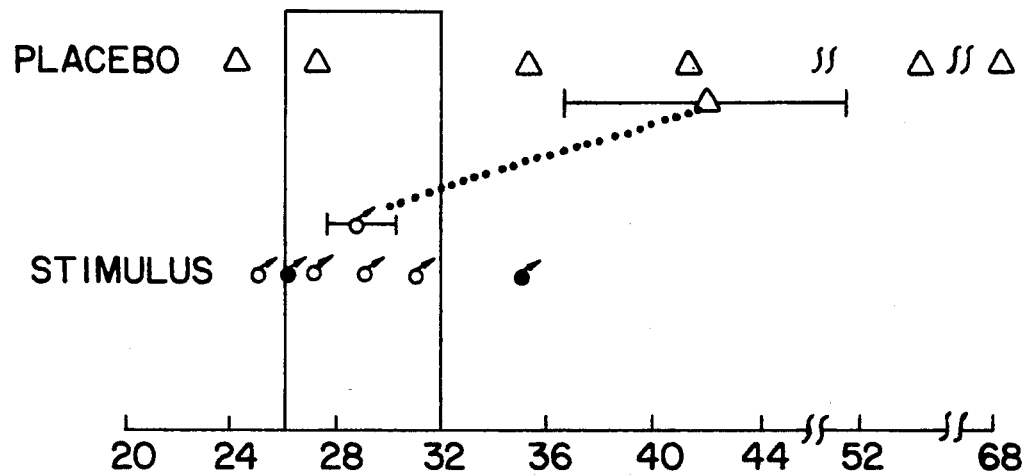

Because weekly heterosexual behavior and 29 day cycles are associated the data for those women who were having weekly sexual activity with men were removed from the data set; the data was then reanalyzed. See Cutler et al. (1980) supra. and Cutler et al. (1979) supra. The results are set forth in FIG. 2. Again, the variances were significantly different (first cycle $F_{6,5}=11.56$, p less than 0.01; last cycle $F_{6,5}=20.61$, p less than 0.01) and although the mean cycle lengths appear to be different, the difference failed to achieve acceptable statistical significance $t=1.645$, 0.05 p less than 0.10. Table 1 shows the incidence of aberrant cycles ( 26 or 33 days) to vary as a function of treatment in all women (left) and when controlled for sexual activity (right). Significance was not achieved until the last cycle. In studying either all the subjects or only those subjects who were not having weekly sexual activity, exposure to male axillary secretions yielded a greater proportion of "normal" (29.5±3 day) cycle lengths than exposure to the placebo.

TABLE 1

INCIDENCE OF ABERRANT CYCLES VARIES AS A FUNCTION OF TREATMENT AND SEXUAL ACTIVITY

| | All Subjects | | | Less than Weekly Subjects | |
|---|---|---|---|---|---|
| | Treatment | | | Treatment | |
| | Extract | Blank | | Extract | Blank |
| | First Cycle | | | | |
| Aberrant cycle | 5 | 7 | Aberrant cycle | 4 | 5 |
| Normal cycle | 2 | 2 | Normal cycle | 2 | 1 |
| | Z = .2936 n.s. | | | Z = .688 n.s. | |

TABLE 1-continued

INCIDENCE OF ABERRANT CYCLES VARIES AS A FUNCTION OF TREATMENT AND SEXUAL ACTIVITY

| | All Subjects | | | Less than Weekly Subjects | |
|---|---|---|---|---|---|
| | Treatment | | | Treatment | |
| | Extract | Blank | | Extract | Blank |
| | | Last Cycle | | | |
| Aberrant cycle | 2 | 6 | Aberrant cycle | 2 | 5 |
| Normal cycle | 5 | 3 | Normal cycle | 4 | 1 |
| | Z = 1.512 | | | Z = 1.754 | |
| | p .066 | | | p .04 | |

The percentage of women exhibiting a normal length luteal phase (at least 12 hyperthermic days) subsequent to receiving the male extract or placebo stimulus has also been determined from basal body temperature charts. Analysis of basal body temperature charts was performed along criteria previously reported. See Cutler et al. (1980) supra. Among all of the women, the sexually active, or the sexually inactive, a higher percentage of male extract recipients than placebo recipients showed a normal length luteal phase basal body temperature graph (p less than 0.0625). See Cutler et al. (1979) supra. The consistency of the results lends credence to them.

Levels of progesterone (3 samples per subject) supported the basal body temperature graph scoring method. In each case were the scorer recorded a presumptively fertile cycle, as well as with presumptive defects in the BBT, the progesterone values were within expected ranges for the days of the cycle assayed. There were no apparent differences in testosterone level, or estradiol level among women who received different treatments or who showed different patterns of sexual activity in this study.

The present invention thus provides a novel method for altering or regulating (normalizing) the length of the menstrual cycle of a human female towards $29.5 \pm 3$ day menstrual cycles, comprising the step of exposing the nasal region of said female to at least a portion of the axillary secretions of the male, said exposure continuing for a duration and being in amounts effective to significantly alter or regulate the expected cycle length of that female While it is presently preferred to use extracts of male axillary secretions as said portions, it is theorized that the effective pheromonal component of the axillary secretions may be one or more of the androgen steroids: androstenol, androstenone, dehydroepiandrosterone, androstadienol, androstadienone dehydroepiandrosterone sulfate (DHAS), androsterone sulfate (AS), and natural derivatives thereof. It is further anticipated that the burnt heavy axillary-like odor component which elutes at about 50 minutes as shown on the FID response curve of FIG. 3B may also exhibit pheromonal activity.

In any event, the portions of the male axillary secretions should be applied periodically for at least two days during each menstrual cycle. Preferably these secretions should be applied three times each week. When application throughout the course of the menstrual cycle is not feasible, it is presently preferred to apply the axillary extract at least during the follicular phase, and preferably also during the periovulatory phase, of the menstrual cycle. As shown from the data collected over the course of several menstrual cycles, application over at least several menstrual cycles is preferred, at least when the male axillary secretions are applied with the frequency and in the concentrations used in this study.

Good results may be obtained when the axillary secretions employed comprise secretions collected from more than one male donor. As mentioned above, it is preferred that such secretion be collected periodically from each male donor and be applied to the upper lip of the female, preferably on a daily basis. When the subject female is being treated for a short menstrual cycle, one in which the luteal phase is 11 days or less, application of the male axillary secretion should continue until luteal phases of at least 12 days are established. A similar regimen should be followed for aberrantly long menstrual cycles, and/or when human females are being treated who exhibit monophasic menstrual cycles as determined from basal body temperature graphs.

The present invention may be practiced by providing a kit for altering the length of the expected menstrual cycle of a human female, comprising a series of medicaments, each of which includes at least a portion of the axillary secretions of a human male donor, whereby the medicaments may be administered periodically to the nasal region of the woman to thereby alter the expected length of that woman's menstrual cycle. A material is thus provided for application to the human body comprising the axillary secretions of at least one, and preferably a plurality, of human male donors Exposure of the woman to subject stimuli may be accomplished through a number of methods. The one described above is clinically acceptable but may be emotionally less preferred. For women who are engaged in a sexual relationship, it may be preferred to apply the stimuli to her partner such that her exposure occurs in a more or less natural manner. Alternatively, other aesthetically pleasing applicators may be developed for the purpose of accomplishing the same purpose.

As mentioned above, the possible role that odors play in human reproductive biology has received considerable attention particularly with respect to the extent to which menstrual synchrony may occur in females who live together. Discussions of male effect on females have often centered on the possibility that odor acts to attract, or sexually arouse the male. The data presented here indicate that prolonged exposure to one or more constituents from the male axillae alters the female endocrine system. Since both the experimental and the control subjects in this study spend a considerable portion of their day in a heterosexual environment, the causative factor in male axillary extract is likely to have a low vapor pressure at body temperature (or none at all) and critical concentrations may only be transferred during intimate contact. While the experimental protocol does not permit definitive determination as to whether the effect is mediated by olfactory stimuli or if the constituents causing the effect are absorbed through the skin, it is nonetheless clear that male extract applied to the nasal region of the treated female definitely effects the female menstrual pattern. These reasons suggest that the active agents in male axillary secretion may be the burnt heavy axillary-like component and/or the steroids mentioned above. As shown in FIG. 3 when using a non-polar silicon phase two main odor-containing areas are seen: one near the solvent front and the second where the volatile steroids (androstenol and androsterone) and pyrolysis products from AS and DHAS elute. The area near the solvent front on the silcon phase is retained longer on the polar CP-57 WAX and elutes with a very marked axillary/burnt odor at approximately 50 minutes into the course of the chromatogram. The steroids do not elute on this columns until well after 70-80 minutes after injection. Many of the short-chain aliphatic acids elute within the first 30 minutes and give sharp, acid-like odors.

Compounds giving rise to the odors eluting from the polar CP-WAX column at approximately 50 minutes may be of particular interest because mass spectrometry of this sample shows no distinct mass spectra in the region where this intense odor is found. Consequently, highly odiferous material exists but its concentration must be below the detection limit of our instrument (at full scan this is approximately 250-500 picograms).

As seen from the above, novel methods for improving the presumptive fertility of human females are disclosed based upon the unexpected discovery that males can exert a "primer" pheromone effect on the human menstrual cycle.

In accordance with an alternate method of the present invention, the aforesaid portion or portions of male axillary secretions may be applied or exposed to the nasal region of females who are experiencing perimenopausal symptoms such as hot flashes, and/or who would like to extend their endocrine regularity and/or longevity. In addition to the evidence set forth above, recent evidence concerning the sexual behavior and steroid levels among gynecologically mature premenopausal women is consistent with the hypothesis that male primer pheromones stimulate production of estrogen by the female endocrine system. As reported in McCoy et al, "Relationships Among Sexual Behavior, Hot Flashes, and Hormone Levels in Perimenopausal Women", Arch Sex Behavior, 14(5):385-394 (1985) which is hereby incorporated by reference as if fully set forth herein, sexual activity is negatively correlated with hot flashes in the perimenopause. Perimenopausal women engaging in sexual intercourse less than once a week have been found to be more likely to have hot flashes than those engaging in regular weekly intercourse. Frequency of sexual intercourse is negatively correlated with level of hot flash rating, the trend being consistent, although significant only at a second interview. A similar negative correlation between estradiol levels and hot flash ratings has also been found. A comparison between women cycling every 30 days (early perimenopausal) with those cycling less frequently (late menopausal) revealed the expected difference in hormone levels and hot flash ratings with estradiol levels significantly lower and the ratio of testosterone to estradiol and the hot flash ratings significantly higher in the late perimenopausal women. The fact that the ratio of testosterone to estradiol significantly increased from the first to the second interview for late women, but showed no change for early women, probably reflects the progression of late women toward the low estradiol level seen with cessation of cycling. The significantly lower rate of sexual intercourse for later as compared with early perimenopausal women is consistent with the significant negative associations obtained between hot flash rating and frequency and regularly of sexual intercourse.

Figure 5:
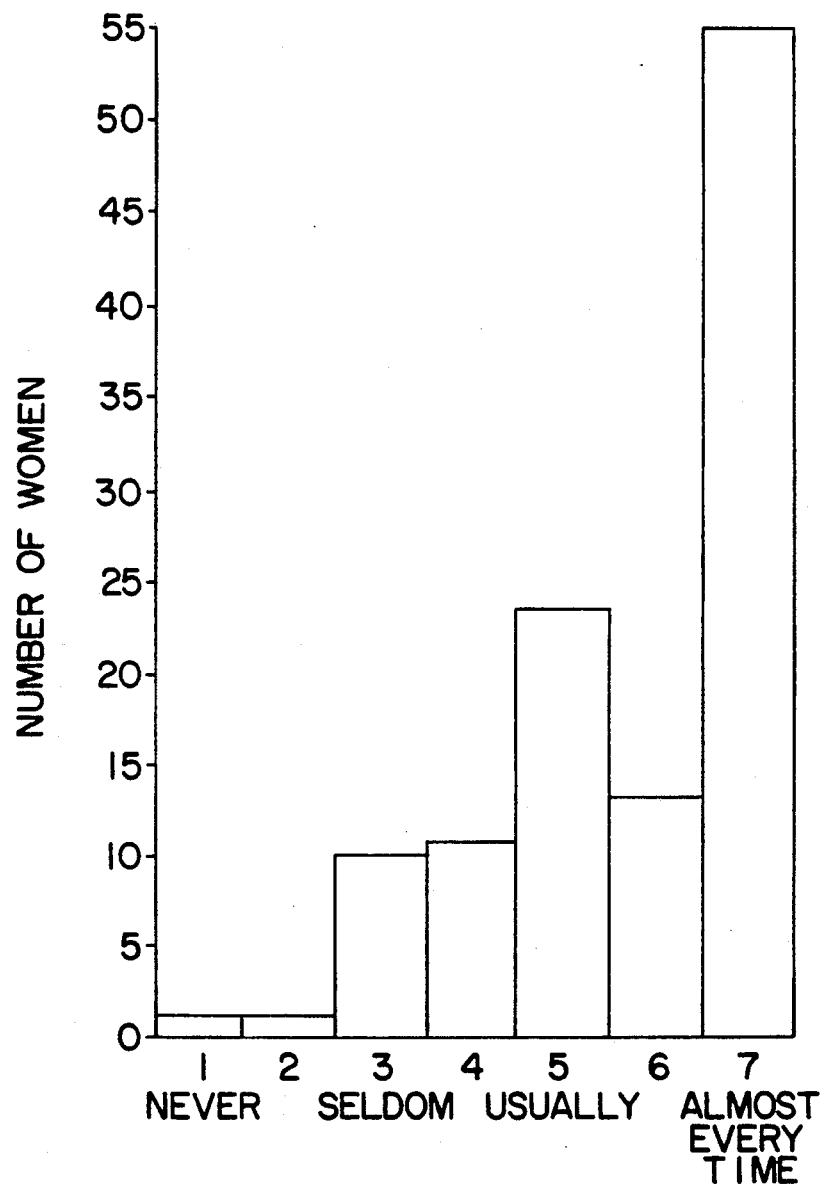
FIG. 5 is a bar graph showing total estrogen (estradiol) levels according to the heterosexual behavior of celibate, sporadic, and at least weekly, gynecologically mature young (22.89 years average age) women.

More recently, sexual behavior and steroid levels among gynecologically mature premenopausal young women have been examined. FIG. 5 reports the estradiol levels of women who were heterosexually active at least on a weekly basis (excluding the week of menses). This figure represents data collected from 27 subjects who participated in a double-blind study. The subjects were recruited from amongst students and office workers, and were paid for their participation. All met the following criteria: gynecologic maturity, nulliparity, not currently (or within the last three months) using oral contraceptives or an IUD, no marijuana or other "pleasure" drugs, and a willingness to make an daily entry of BBT, sexual behavior and menstrual occurrence.

The subjects were screened for possible pathologic factors that might influence the length of the menstrual cycle, and none were found. Of 44 women originally enrolled, 9 of 28 aberrant cyclers dropped out of the study before supplying blood samples and 5 supplied samples too late in the study for evaluation of where within a BBT cycle they had occurred. Of 16 self-reported, approximately 29-day cyclers, two dropped out before supplying blood and one supplied blood too late for evaluation. The study began Sep. 1, 1983 and was scheduled to be completed by Dec. 15, 1983. Further details of the experimental protocol and data appear in Cutler et al, "Sexual Behavior and Steroid Levels Among Gynecologically Mature Premenopausal Women", Fertil Steril (April, 1986), which is hereby incorporated by reference as if fully set forth herein. In this study, the possibility of a correlation between heterosexual total and each of the steroids was tested, but none was found. Consequently, total coital activity of a woman throughout the duration of the study was not related to her sex steroid hormone level. This is consistent with data obtained in the aforementioned study of perimenopausal women, and is consistent with the explanation that sex steroid levels are elevated as a result of exposure to at least threshold level of pheromone.

Accordingly, this study suggests that women who have regular weekly sex with men have higher levels of estrogen than women who do not. Furthermore, it also suggests that the total amount of coital events is not relevant to the steroid level, whereas the consistency of the behavior is relevant. Although this result was implied by earlier work on perimenopausal women, this is the first study in which hormone levels are concomitantly evaluated with the behavior and cycle length of women of reproductive age.

A further study was conducted to investigate female sexuality during the perimenopause. This study included results of 52 women's prospective coital behavior records and concomitant steroid analyses when a later contact with the subjects was conducted approximately three months later. In order to qualify for participation in this study, women had to have a menstrual cycle within the last two years, but to have found an increasing irregularity either in length of cycle or pattern of flow. At the third interview, women reported varying intervals since the last menstrual period, 56 having had a menses within the last thirty days, 20% within the last sixty days, 9% within the last six months, 3% within the last 12 months, 5% within the last 18 months and 5% within the last 24 months. 71% reported the occurrence of hot flashes among their symptoms. 12% were experiencing night sweats as well. Only three women had used estrogen replacement therapy at least two months prior to the entry of the study. The educational level of the sample averaged 14.86±0.19 years (2 years of college) The age distribution of the sample ranged between 33 and 56 with the mean 48.67±0.34 years. The heaviest concentration of subjects ranged between 44 and 52 years. Menarche occurred at 12.7±or 0.12 years. Pregnancy rate averaged 3.24±0.16, life birth incidence 2.44±0.13, and length of marriage, an average 20.8 years.

Figure 4:
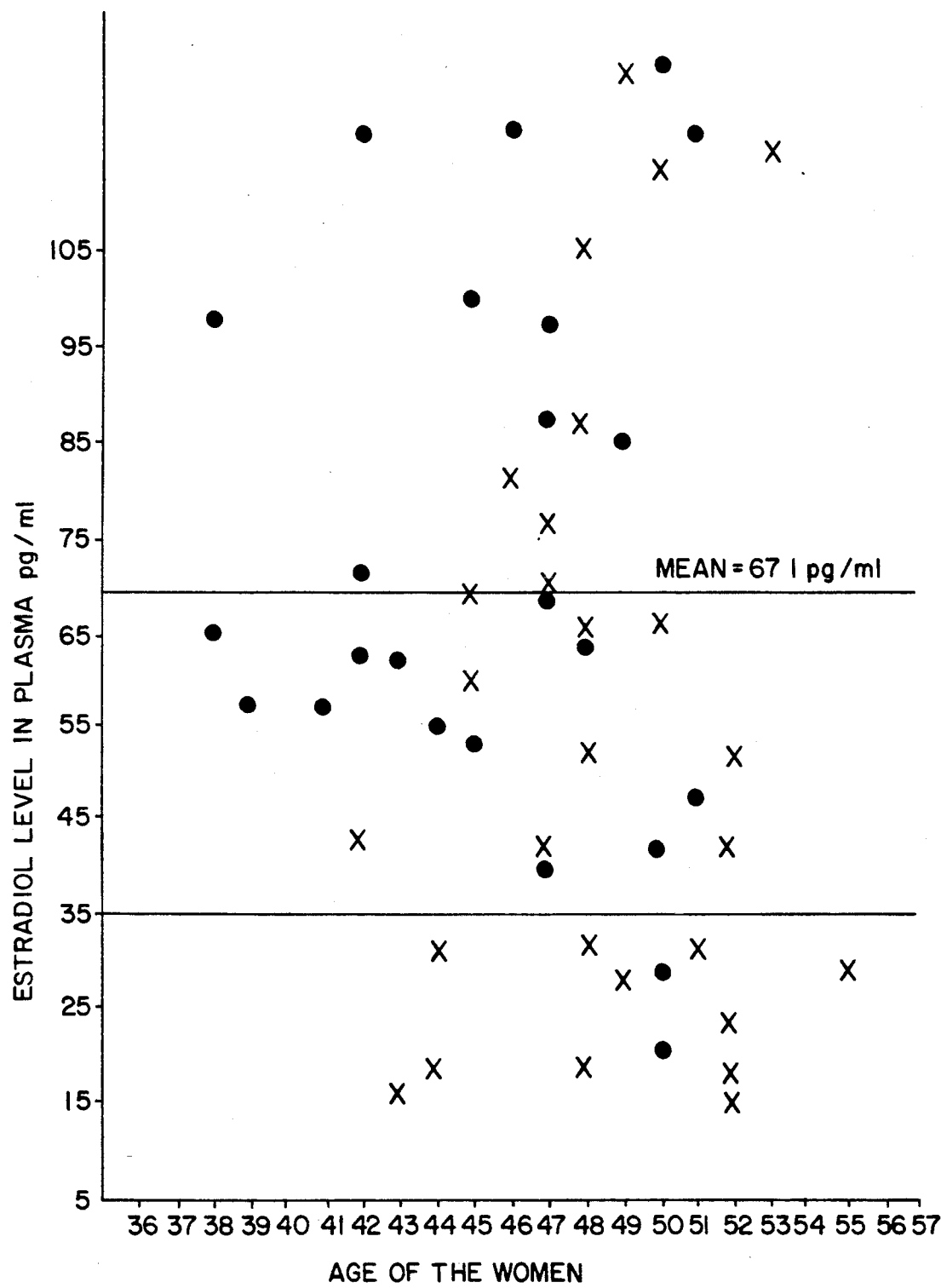
FIG. 4 is a chart of data showing circulating estrogen (estradiol) levels in gynecologically mature women correlated to their sexual frequency and age.

Sexual frequency data were collected prospectively using calendars such as those described in Cutler, Garcia and Krieger . (1979) or Cutler Preti et al (1985). Blood samples drawn from the subjects were separated and the plasma frozen and later tested by radioimmunoassay for levels of estradiol and testosterone. Mean inter-assay coefficients of variations were: estradiol 9.7 and testosterone 7.8; the intra-assay coefficients were 13.5 and 6.9 respectively. FIG. 4 arrays the estradiol level in each woman and indicates her age as well as her sexual frequency category. X=less than week, O=at least once a week. The age distribution of the sample and the apparent lack of relationship in this perimenopausal sample, between age and estradiol level should be noted. For those women who were still menstruating, on the month of the plasma drawing, plasma samples were drawn during the first five days of the cycle - when estradiol is at its cyclic lowest. In FIG. 4, the line is drawn at 35 pg/ml because this is a commonly understood menopausal estradiol level, and is lower than generally found on any of the days of the normal menstrual cycle. When one examines the data array, it will be seen that the estradiol levels that were below 35 pg/ml show an increased proportion of less than weekly active women ($z=2.57$ $p=0.005$, test of proportions; Dixon and Massey 1969). Women whose estrogen levels reach this nadir are considered hormonally postmenopausal.

These results suggest that among the subset of women whose estradiol levels are clearly in the menopausal range, there is an increased proportion of women showing less than weekly sexual activity. This result is concordant with the aforementioned report showing a "close association . . . between . . . declining estradiol levels and declining frequency of intercourse during the perimenopause". It also confirms the phenomena previously referred to in the sample of young women showing that less than weekly patterns of heterosexual behavior show significantly lower estrogen levels, whereas women with estradiol levels below 40 pg/ml tended to be less than weekly sexually active.

The results of the aforementioned studies indicate that the effects of regulating the human menstrual cycle achieved by the application of male axillary secretion extracts with younger women will be equally as applicable to their older, perimenopausal counterparts. It is theorized that such applications are, in endocrinologic terms, functional substitutes for weekly sex with a male partner. Such exposure is believed to increase circulating levels of estradiol, to thus counteract otherwise expected menopausal symptoms.

What is claimed is:

1. A method for altering or regulating the length of the menstrual cycle of a woman not having a normal 29∓3 day menstrual cycle towards a 29±3 day menstrual cycle, comprising the steps of (a) selecting at least one component but less than all of the components of the axillary secretions of at least one man, said at least one component being effective to so alter or regulate the menstrual cycle length of a woman whose nasal region is exposed to said component; and (b) exposing the nasal region of said woman to said at least one component in an amount and for a direction effective to so alter or regulate said woman's menstrual cycle.

2. A method for treating a menopausal symptom in a menopausal woman exhibiting such symptom comprising the steps of (a) selecting at least one component but less than all of the components of the axillary secretions of at least one man, said at least one component being effective to reduce the frequency of said symptom in a menopausal woman whose nasal region is exposed to said component; and (b) exposing the nasal region of said woman to said at lest one component in an amount and for a duration effective to so reduce the frequency of occurrence of said symptom in said woman.

3. The method of claims 1 or 2 wherein said at least one component is selected to comprise androstenol.

4. The method of claims 1 or 2 wherein said at least one component is selected to comprise dehydroepiandrosterone sulfate.

5. The method of claims 1 or 2 wherein said at least one component is selected to comprise at least one compound selected from the group consisting of androstenol, adrostenone, dehydroepiandrosterone, dehydroepiandrosterone sulfate, androstadienol, androstadienone, androsterone sulfate and natural derivatives thereof.

6. The method of claims 1 or 2 wherein said at least one component of said axillary secretions include the component of said secretions exhibiting a burnt heavy axillary-like odor which elutes at about 50 minutes as shown in the FID response curve of FIG. 3B.

7. The method of claim 1 where said at least one component is applied periodically for at least two days during each menstrual cycle.

8. The method of claim 7 wherein said at least one component is applied periodically over the course of at least two menstrual cycles.

9. The method of claims 1 or 2 wherein said man has a population of lipophilic diptheroid bacteria in his axillary region.

10. The method of claims 1 or 2 wherein said secretions comprise secretions collected from more than one man.

11. The method of claims 1 or 2 wherein said at least one component is applied to the upper lip or the skin region between the nose and upper lip of said woman.

12. The method of claim 11 wherein said at least one component is applied at least weekly to the upper lip of said woman.

13. The method of claim 1 wherein said woman has an expected menstrual cycle exhibiting a luteal phase of less than 12 days and wherein said exposing is continued until the luteal phase of the menstrual cycle has lengthened to at least 12 days.

14. The method of claim 2 wherein said symptom is selected from hot flashes, night sweats and irregular menstrual cycles.

15. The method of claim 1 wherein said exposing step comprises exposing said at least one component to said female at periodic times during each menstrual cycle.

16. The method of claim 14 wherein said periodic times are in at least four separate days of said cycle.

17. The method of claim 16 wherein said periodic times are spaced apart on days throughout at least the follicular and periovulatory phases of each cycle.

18. The method of claim 17 wherein said times include at least times during each of the cycle day period 1-6, 7-12, 13-18, and 19-menses wherein cycle day 1 is the first day of menstruation.

* * * * *

UNITED STATES PATENT AND TRADEMARK OFFICE
CERTIFICATE OF CORRECTION

PATENT NO. : 5,155,045
DATED : October 13, 1992
INVENTOR(S) : Cutler et al

It is certified that error appears in the above-indentified patent and that said Letters Patent is hereby corrected as shown below:

On title page, under "OTHER PUBLICATIONS"
Column 2, Below "M. K. McClintock, "Menstrual Synchrony and Suppression", Nature, 229:244-245 (Jan., 22, 1971)." insert --A Textbook in Medicine, edited by Cecil 5th ed. WB Saunders Co., Philadelphia, 1941, p. 673-5.

C. A. Graham et al "Menstrual Synchrony in Female Undergraduates Living on a Coeducational Campus", Psychoneuroendocrinology, 5: 245-252 (1980).

Rogel, "A Critical Evaluation of the Possibility of Higher Primate Reproductive and Sexual Pheromones", Psychol. Bull. 85: 810-830, (1978).

D.M. Quadagno, "Influence of Male Social Contacts, Exercise and All-Female Living Conditions on the Menstrual Cycle" Psychoneuroendocrinology, 6: 239-244 (1981).

J. L. Veith et al, "Exposure to Men Influences in the Occurrence of Ovulation in Women", Physiology & Behavior, 31: 313-315 (1983).

Russell et al "Olfactory Influences on the Human Menstrual Cycle", Pharmac. Biochem. Behav., 13(5): 1-2 (1980).

UNITED STATES PATENT AND TRADEMARK OFFICE
CERTIFICATE OF CORRECTION

PATENT NO. : 5,155,045
DATED : October 13, 1992
INVENTOR(S) : Cutler et al.

It is certified that error appears in the above-identified patent and that said Letters Patent is hereby corrected as shown below:

J. N. Labows, "Human Odors - What Can They Tell Us?", Perfumer and Flavorist, 4: 12-17 (1979).

J.J. Leyden et al "The Microbiology of the Human Axilla and Its Relation to Axillary Odors", J. Invest. Dermatol. 77:413-416 (1981).

S. Bird et al, "Axillary 5δandrost-16-en-3-one, Cholesterol and Squalene in Men; Preliminary Evidence for 5δandrost-16-3n-3-one Being a Product of Bacterial Action", J. Steroid Biochem., 17: 517-522 (1982).

S. Bird et al, "Measurement of 5δandrost-16-en-one in Human Axillary Secretions by Radioimmunoassay", J. Endrocrinol., 85: 80-90.

B.W.L. Brooksbank et al, "The Detection of 5δandrost-16-en-3δol in Human Male Axillary Sweat", Experientia, 30: 864-865 (1974).

R.V. Vollman, The Menstrual Cycle, Vol. 7, (Major Problems in Obstetrics and Gynecology), edited by Emmanuel Freidman, M.D.

A.E. Treloar, "Variation of the Human Menstrual Cycle Through Reproductive Life", Internl Journl of Fert., 12(1):77-126 (1967).

W. Cutler, "Lunar and Menstrual Phase Locking", American Journal of Obstetrics and Gynecology, 137: 834 (1980).

W. Cutler et al, "Infertility and Age at First Coitus: A Possible Relationship" J. Biosoc. Sc., 11:425-432 (1979).

UNITED STATES PATENT AND TRADEMARK OFFICE
CERTIFICATE OF CORRECTION

PATENT NO. : 5,155,045
DATED : October 13, 1992
INVENTOR(S) : Cutler et al.

It is certified that error appears in the above-identified patent and that said Letters Patent is hereby corrected as shown below:

W. Cutler et al, "Sexual Behavior Frequency and Menstrual Cycle Length in Mature Premenopausal Women", Psychoneuroendocrinology, 4:297-309 (1979).

W. Cutler et al, "Luteal Phase Defects: A Possible Relationship Between Short Hyperthermic Phase and Sporadic Sexual Behavior in Women", Hormones and Behavior, 13:214-218 (1979).

W. Cutler et al, "Sporadic Sexual Behavior and Menstrual Cycle Length in Women". Hormones and Behavior, 14: 163-172 (1980).

W. Cutler et al, "The Psychoneuroendocrinology of the Ovulatory Cycle of Woman: A Review", Psychoneuroendocrinology, 5:89 (1980).

W. Cutler et al, "Sexual Behavior, Steroids & Hot Flashes are Associated During the Perimenopause", Neuroendocrinology Letters, 5:185 (1983).

J. N. Labows et al, "Steroid Analysis of Human Apocrine Secretion", Steroids, 34:249-258 (1979).

G. Preti et al, "Cyclic Changes in Volatile Acidic Metabolites of Human Vaginal Secretions and Their Relationships to Ovulation", J. Chem. Ecol, 1:361-376 (1975).

Frolich et al, "Serum Levels of Unconjugated Aetiocholanolone, Androstenedione, Testosterone, Dehydroepiandrosterone, Aldosterone, Progesterone and Oestrogens During the Normal Menstrual Cycle", Acta Endocrinologica, 81:548-562 (1976).

UNITED STATES PATENT AND TRADEMARK OFFICE
CERTIFICATE OF CORRECTION

PATENT NO. : 5,155,045          Page 4 of 7
DATED : October 13, 1992
INVENTOR(S) : Cutler et al.

It is certified that error appears in the above-identified patent and that said Letters Patent is hereby corrected as shown below:

Abstract presented at the CRB Conference on Reproductive Behavior June 10-12, 1984 at the University of Pittsbrugh, entitled "Sex Frequency and Human Axillary Secretion Influence Fertile-Type Menstrual Cycles".

"Male Extract and Heterosexual Behavior Normalize the Menstrual Cycle of Women", Abstract, International Academy of Sex Cambridge, England (September, 1984), Cutler et al.

A. R. Genazzani et al, "Possible Correlation Between Plasma Androgen Variations During the Menstrual Cycle and Sexual Behavior in the Human Female", Chemical Abstracts, Vol. 91, 1978, Abstract No. 91: 121339e, Proc. Serono Symp. 22(Clin. Psychoneuroendo. Reprod. 419-435.

N. McCoy et al, "Relationships Among Sexual Behavior, Hot Flashes, and Hormone Levels in Perimenopausal Women", Archives of Sexual Behavior, 14(5):385-394 (1985).

Cutler et al, "The Medical Management of Menopause and Premenopause" Chapter 3, J.B. Lippincott Company, pp. 92-121 (1984).

"New Nose to Aid Fertility", Daily News, October, 1984.

Bahn, Basic Medical Statistics, Chapter 8, "Review of the Decision Making Process; the Error Risks", p. 86, (1972) Grune & Stratton, Inc.

Cutler et al, "Sexual Behavior and Steroid Levels Among Gynecologically Mature Premenopausal Women", Fertil. & Steril, April, 1986.

UNITED STATES PATENT AND TRADEMARK OFFICE
CERTIFICATE OF CORRECTION

PATENT NO. : 5,155,045
DATED : October 13, 1992
INVENTOR(S) : Cutler et al.

It is certified that error appears in the above-identified patent and that said Letters Patent is hereby corrected as shown below:

Cutler et al, "Perimenopausal Sexuality", <u>Archives of Sexual Behavior</u> (in press).

C.C. Norris, "The Menopause", <u>American Journal of Obstet.</u>, <u>41</u>:203-215 (1910).

Metcalf, "Incidence of Ovulatory Cycles in Women Approaching the Menopause", <u>Journal of Biosoc. Sci.</u>, <u>11</u>:39-48 (1979).

Rutherford, "The Menopause", <u>N.Z. Med. J.</u>, <u>87</u>:251-253 (1978).

Kupperman et al, "Contemporary Theory of the Menopausal Syndrome", <u>JAMA</u>, <u>171</u>:1627-1637 (1959)--
On title page;
Under "*Primary Examiner*-F.T. Moezie" insert --*Attorney, Agent, or Firm*-Woodcock, Washburn, Kurtz, Mackiewicz & Norris--

Column 3, Line 32 delete "McClintoc" and insert therefor --McClintock--.

Column 3, Line 34 delete "Enhancemen" and insert therefor --Enhancement--.

Column 3, Line 66 delete "of woman" and insert therefor --of women--.

Column 6, Line 50 delete "Microccaceae" and insert therefor --Micrococcaceae--.

Column 7 Lines 2-3 delete "Radioimmunosassary"," and insert therefor --Radioimmunoassay",--

Column 7 Line 5 delete " -androst-16-en-3 ol" and insert therefor -- -androst-16-en-3-ol--.

UNITED STATES PATENT AND TRADEMARK OFFICE
CERTIFICATE OF CORRECTION

PATENT NO. : 5,155,045
DATED : October 13, 1992
INVENTOR(S) : Cutler et al.

It is certified that error appears in the above-identified patent and that said Letters Patent is hereby corrected as shown below:

Column 7 Line 7 delete "where" and insert therefor --were--.

Column 7 Line 68 delete "Psychoneuroendochrinology" and insert therefor --Psychoneuroendocrinology--.

Column 8, Line 3 delete "ad" and insert therefor --and--.

Column 9, Line 49 delete "liability" and insert therefor --lability--.

Column 10, Lines 11-12 delete "*Psychoneuroendocrinology*, 297-309" and insert therefor --*Psychoneuroendocrinology*, 4: 297-309--

Column 11, Line 53 delete "body- comprising" and insert therefor --body comprising--.

Column 13 Line 9 delete "E. Labows," and insert therefor --E., Labows,--.

Column 13 Line 11 delete "sections" and insert therefor --secretions--.

Column 13 Line 44 delete "study All" and insert therefor --study. All--.

Column 15, Line 30 delete "were" and insert therefor --where--.

Column 15, Line 46 delete "female While" and insert therefor --female. While--.

UNITED STATES PATENT AND TRADEMARK OFFICE
CERTIFICATE OF CORRECTION

PATENT NO. : 5,155,045
DATED : October 13, 1992
INVENTOR(S) : Cutler et al.

It is certified that error appears in the above-identified patent and that said Letters Patent is hereby corrected as shown below:

Column 17, Line 58 delete "later" and insert therefor --late--.

Column 17, Line 61 delete "regularly" and insert therefor --regularity--.

Column 18, Line 7 delete "an daily" and insert therefor --a daily--.

Column 19, Line 6 delete "Krieger. (1979)" and insert therefor --Krieger (1979)--.

Column 19, Line 58 delete "29∓3" and insert therefor --29±3--.

Column 19, Line 66 delete "direction" and insert therefor --duration--.

Column 20, Line 58 delete "claim 14" and insert therefor --claim 15--.

Column 20, Line 64 delete "period" and insert therefor --periods--.

Signed and Sealed this

Eighth Day of February, 1994

BRUCE LEHMAN

*Attest:*

*Attesting Officer*                *Commissioner of Patents and Trademarks*

UNITED STATES PATENT AND TRADEMARK OFFICE
CERTIFICATE OF CORRECTION

PATENT NO. : 5,155,045

DATED : October 13, 1992

INVENTOR(S) : Cutler et al.

It is certified that error appears in the above-identified patent and that said Letters Patent is hereby corrected as shown below:

On title page, item [73] add the following: --Monell Chemical Senses Center, Philadelphia, Pa.--

Signed and Sealed this

Third Day of May, 1994

Attest:

BRUCE LEHMAN

Attesting Officer

Commissioner of Patents and Trademarks